(12) United States Patent
Paul et al.

(10) Patent No.: US 7,829,514 B2
(45) Date of Patent: Nov. 9, 2010

(54) DETERGENT COSMETIC COMPOSITIONS COMPRISING FOUR SURFACTANTS, A CATIONIC POLYMER, AND A BENEFICIAL AGENT AND USES THEREOF

(75) Inventors: Laurence Paul, Saint leu la Foret (FR); Franck Giroud, Chamoux sur Gelon (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/213,933

(22) Filed: Jun. 26, 2008

(65) Prior Publication Data

US 2009/0048132 A1    Feb. 19, 2009

Related U.S. Application Data

(60) Provisional application No. 60/929,602, filed on Jul. 5, 2007.

(30) Foreign Application Priority Data

Jun. 29, 2007    (FR) .................................. 07 56160

(51) Int. Cl.
| | |
|---|---|
| C11D 1/02 | (2006.01) |
| C11D 1/88 | (2006.01) |
| C11D 3/22 | (2006.01) |
| C11D 3/37 | (2006.01) |
| C11D 3/382 | (2006.01) |
| A61K 8/73 | (2006.01) |

(52) U.S. Cl. .................. 510/119; 510/123; 510/125; 510/127; 510/151; 510/155; 510/156; 510/426; 510/433; 510/474; 510/475; 510/490; 510/492; 510/504; 424/70.5; 424/70.11; 424/70.13; 424/70.21; 424/70.22

(58) Field of Classification Search ................. 510/119, 510/123, 125, 127, 151, 155, 156, 426, 433, 510/474, 475, 490, 492, 504; 424/70.5, 70.11, 424/70.13, 70.21, 70.22
See application file for complete search history.

(56) References Cited

U.S. PATENT DOCUMENTS

| 5,449,475 A | 9/1995 | Cauwet et al. |
|---|---|---|
| 5,661,118 A | 8/1997 | Cauwet et al. |
| 7,514,091 B2 | 4/2009 | Restle et al. |
| 2006/0275245 A1 | 12/2006 | Decoster et al. |

FOREIGN PATENT DOCUMENTS

| DE | 43 02 314 A1 | 8/1994 |
|---|---|---|
| DE | 44 09 189 A1 | 9/1995 |
| DE | 197 23 763 A1 | 12/1998 |
| DE | 19723763 | * 12/1998 |
| DE | 19723763 C2 | * 12/1998 |
| EP | 0 603 078 A | 6/1994 |
| EP | 0 974 335 A1 | 1/2000 |
| EP | 1 321 124 A2 | 6/2003 |
| EP | 1 661 976 A1 | 5/2006 |
| EP | 1661976 | * 5/2006 |
| EP | 1 726 293 A1 | 11/2006 |
| FR | 2 718 961 | 10/1995 |
| WO | WO 9733561 | 9/1997 |

OTHER PUBLICATIONS

English Abstract for EP 1 321 124, Jun. 25, 2003.
English Abstract for DE 43 02 314, Aug. 4, 1994.
English Abstract for DE 197 23 763, Dec. 10, 1998.
English Abstract for DE 44 09 189, Sep. 21, 1995.
French Search Report for FR 0756160, Apr. 2, 2008.

* cited by examiner

*Primary Examiner*—Brian P Mruk
(74) *Attorney, Agent, or Firm*—Finnegan, Henderson, Farabow, Garrett & Dunner, LLP

(57) ABSTRACT

The disclosure relates to novel detergent and conditioning compositions comprising, in a cosmetically acceptable aqueous medium, (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, and (F) at least one beneficial agent other than the at least one cationic polymer of (E), wherein the sulfate, sulfonate or phosphate anionic surfactant/amphoteric surfactant weight ratio is in a range from 0.1 to 2. Also disclosed are uses of said composition for cleansing and caring for the hair or the skin.

22 Claims, No Drawings

DETERGENT COSMETIC COMPOSITIONS COMPRISING FOUR SURFACTANTS, A CATIONIC POLYMER, AND A BENEFICIAL AGENT AND USES THEREOF

This application claims benefit of U.S. Provisional Application No. 60/929,602, filed Jul. 5, 2007, the contents of which are incorporated herein by reference. This application also claims benefit of priority under 35 U.S.C. §119 to French Patent Application No. FR 0756160, filed Jun. 29, 2007, the contents of which are also incorporated herein by reference.

The present disclosure relates to novel detergent cosmetic compositions for keratin materials, for example for human keratin materials such as the hair, comprising, in a cosmetically acceptable aqueous support, at least one sulfate, sulfonate or phosphate anionic surfactant, at least one carboxylic anionic surfactant other than the preceding surfactant, at least one amphoteric surfactant, and at least one nonionic surfactant of alkylpolyglycoside type. The disclosure also relates to the use of said compositions in the abovementioned cosmetic application.

It is well known that hair is sensitized or embrittled to varying degrees by the action of atmospheric agents and especially light, water and humidity, and also by repeated mechanical or chemical treatments such as brushing, combing, washing, bleaching, permanent-waving, relaxing and/or dyeing. Numerous publications disclose that natural light destroys certain amino acids of the hair. These attacking factors impair the hair fibers and reduce their mechanical properties, for instance their tensile strength, breaking load and elasticity, or their resistance to swelling in an aqueous medium. The hair is dull, coarse and brittle. It is difficult to disentangle and to style.

It is also known that light and washing agents have a tendency to attack the natural color of the hair and also the artificial color of dyed hair. The hair color gradually fades or turns toward unaesthetic or undesirable shades.

Substances for protecting the hair against the degradation caused by atmospheric attacking factors, such as light and heat, and treatments, have been sought for many years in the cosmetics industry. For example, products that improve the cosmetic properties (such as the disentangling, softness, smoothness, sheen, etc.) and products that protect the color of naturally colored or artificially dyed keratin fibers and that preserve or reinforce the intrinsic mechanical properties of keratin fibers (their tensile strength, breaking load and elasticity, or their resistance to swelling in an aqueous medium) are sought.

Moreover, the skin may also be impaired to varying degrees by the action of atmospheric agents and also by the repeated action of detergent products. The skin tissue may be burnt, and the skin becomes dry and coarse and loses its natural elasticity. The appearance of dandruff, of excess seborrhea or, conversely, of excess dryness may then be observed.

It is known practice to protect the hair and the skin from the effects of light by applying thereto water-soluble or water-insoluble, polymeric or nonpolymeric UV-screening agents, nanoparticles, antioxidants, metal-complexing or chelating agents, or free-radical scavengers.

For better disentangling and prevention of coarseness of the hair, water-soluble or water-insoluble monomeric or polymeric conditioning agents may also be applied thereto.

The compositions of the prior art may allow the problems mentioned to be solved to a certain extent, but their use is unsatisfactory. The reason for this is that repeated applications of these compositions often have the effect of giving the hair an unpleasant feel, loss of volume and liveliness of the head of hair, and occasionally loss of sheen. Moreover, such compositions may produce a persistent greasy feel on the skin.

In the field of "rinse-out" cosmetic compositions, such as shampoos, shower gels, facial makeup removers and shaving foams, detergent compositions comprising agents that are beneficial to the hair or the skin are known. These beneficial ingredients can be introduced into the composition to facilitate the disentangling of the hair, to improve the feel qualities of the keratin fiber or of the skin, or else to promote the moisturization of the latter. In this context, cationic polymers, silicones and emollients such as polyols are the ingredients most commonly used.

To obtain the intended beneficial effect, it is necessary to introduce into the rinse-out composition an amount of beneficial agent much greater than that required to obtain the effect. For rinse-out detergent compositions, the majority of the beneficial agent is in fact removed during the rinsing of the composition, and the effective part of the agent contained in the composition is consequently very small.

However, at the time of invention, no rinse-out detergent compositions exist that can substantially increase the amount of beneficial agent vectorized after rinsing. Such compositions would make it possible to use much less beneficial agent to provide the same level of beneficial effect.

Applicants have discovered, surprisingly, that by using, in a cosmetically acceptable medium, at least one combination of four surfactants and at least one particular cationic polymer in combination with at least one agent that is beneficial to keratin materials, the drawbacks mentioned above may be overcome.

For example, it may be possible to increase the deposition of the beneficial agent on the keratin materials and thereby to increase the efficacy of said beneficial agents or to reduce the amount of said agent used.

One aspect of the present disclosure is thus a detergent cosmetic composition, wherein it comprises, in a cosmetically acceptable aqueous medium, (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, and (F) at least one agent that is beneficial to keratin materials other than the at least one cationic polymer of (E), wherein the sulfate, sulfonate or phosphate anionic surfactant/amphoteric surfactant weight ratio is in a range from 0.1 to 2.

Without wishing to limit the present disclosure to any theory, it would appear that, during rinsing, there are particular interactions and/or affinities between the agent that is beneficial to keratin materials, the combination of surfactants in accordance with the disclosure, the cationic polymer and the hair, which promote uniform, substantial and long-lasting deposition of said agents that are beneficial to keratin materials and of the cationic polymer on the surface of said hair, this qualitative and quantitative deposition may be one of the causes of the improvement observed with regard to the final properties, for example the ease of styling, the disentangling, the smoothness, the softness and the sheen of the treated hair when a conditioning agent is used.

All these discoveries form the basis of the present disclosure.

Another aspect of the present disclosure concerns the use of at least one combination comprising (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, wherein the sulfate, sulfonate or phosphate anionic surfactant/amphoteric surfactant weight ratio is in a range from 0.1 to 2, in, or for the manufacture of, a cosmetic composition comprising at least one agent that is beneficial to keratin materials.

An aspect of the present disclosure is also the use of at least one combination comprising (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, wherein the sulfate, sulfonate or phosphate anionic surfactant/amphoteric surfactant weight ratio is in a range from 0.1 to 2, in a composition comprising at least one agent that is beneficial to keratin materials, for increasing the efficacy of the at least one agent that is beneficial to keratin materials.

Another aspect of the present disclosure is the use of at least one combination comprising (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, wherein the sulfate, sulfonate or phosphate anionic surfactant/amphoteric surfactant weight ratio is in a range from 0.1 to 2, in a composition comprising at least one agent that is beneficial to keratin materials, for improving the deposition and/or fixing of said at least one agent on the keratin materials.

A further aspect of the present disclosure is the cosmetic use of the above compositions for cleansing and/or removing makeup from and/or conditioning keratin materials such as the hair and the skin.

All the meanings and definitions of the compounds used in the present disclosure given below are valid for all of the aspects of the present disclosure.

According to the present disclosure, the term "at least one" means "one", "two", "three" . . . or more.

An agent that is beneficial to keratin materials is an agent that is capable of protecting, enhancing, conditioning, treating, and/or facilitating the shaping of keratin materials, such as the hair.

(A) Anionic Surfactants Comprising at Least One Group Chosen from Sulfate, Sulfonate and Phosphate According to the present disclosure, the at least one anionic surfactant comprising at least one group chosen from sulfate, sulfonate and phosphate are anionic surfactants comprising at least one sulfate ($-OSO_3H$ or $-OSO_3^-$) function and/or at least one sulfonate ($-SO_3H$ or $-SO_3^-$) function and/or at least one phosphate function.

Non-limiting examples of the sulfate and sulfonate anionic surfactants that may be used, alone or as mixtures, in the context of the present disclosure are salts (for example, alkali metal salts, such as salts of sodium, ammonium salts, amine salts, amino alcohol salts, and magnesium salts) of alkyl sulfates, alkylamido sulfates, alkyl ether sulfates, alkylamido ether sulfates, alkylaryl ether sulfates, alkyl ether sulfosuccinates, acyl isethionates and methyl acyl taurates. The alkyl and acyl radicals of all these various compounds in at least one embodiment, comprise from 8 to 24 carbon atoms, and the aryl radical, in at least one embodiment, is chosen from phenyl and benzyl groups.

The average number of ethylene oxide or propylene oxide groups may, in at least one embodiment, range from 2 to 50, such as from 2 to 10.

Among these anionic surfactants, in at least one embodiment, ($C_8$-$C_{14}$)alkyl ether sulfate salts, such as ($C_{12}$-$C_{14}$)alkyl ether sulfate salts, are used. These salts, in at least one embodiment, comprise from 2 to 5 ethylene oxide groups.

Additional non-limiting examples of anionic surfactants used in at least one embodiment include sodium, triethanolamine, magnesium or ammonium ($C_{12}$-$C_{14}$)alkyl sulfates, sodium, ammonium or magnesium ($C_{12}$-$C_{14}$)alkyl ether sulfates oxyethylenated with 2.2 mol of ethylene oxide, sodium cocoylisethionate and methyltaurates. Sodium cocoyl isethionate and methyl acyltaurates may also be used as sulfate or sulfonate anionic surfactants.

The sulfate, sulfonate or phosphate anionic surfactants can be present in an amount ranging from 1% to 50% by weight, for example from 2% to 25% by weight, from 3% to 20% by weight, from 3% to 10% by weight, or from 3.5% to 8% by weight, relative to the total weight of the composition.

(B) Carboxylic Anionic Surfactants

According to the present disclosure, the at least one carboxylic anionic surfactant other than the at least one anionic surfactant of (A) is chosen from anionic surfactants comprising at least one carboxylic function ($-COOH$) optionally in salt form ($-COO^-$).

The at least one anionic surfactant of carboxylic type other than the at least one surfactant of (A), in at least one aspect of the disclosure, comprises no sulfate or sulfonate functions and may be chosen from, but are not limited to, alkyl D-galactoside uronic acids and salts thereof, polyoxyalkylenated ($C_6$-$C_{24}$)alkyl ether carboxylic acids, polyoxyalkylenated ($C_6$-$C_{24}$)alkylaryl ether carboxylic acids and salts thereof, polyoxyalkylenated ($C_6$-$C_{24}$)alkylamido ether carboxylic acids and salts thereof, such as those comprising from 2 to 50 alkylene oxide groups, for example ethylene oxide, such as the compounds sold by the company Kao under the name AKYPO®, ($C_6$-$C_{24}$)acyl sarcosinates and salts thereof, ($C_6$-$C_{24}$)acyl lactylates and salts thereof, and ($C_6$-$C_{24}$)acyl glutamates. ($C_6$-$C_{24}$)Alkylpolyglycoside carboxylic esters such as alkylglucoside acetates, alkylglucoside citrates and alkylpolyglycoside tartrates may also be used. Such products are sold, for example, under the names EUCAROL® APG/EC and EUCAROL® APG/ET by the company Lamberti, and PLANTAPON® LGC Sorb by the company Cognis.

Mixtures of these surfactants may also be used.

The salts are chosen, in at least one aspect of the disclosure, from alkali metal salts, such as of sodium, ammonium salts, amine salts, salts of amino alcohols, such as triethanolamine or monoethanolamine, and magnesium salts.

In at least one embodiment, polyoxyalkylenated ($C_6$-$C_{24}$) alkyl ether carboxylic acids and salts thereof, polyoxyalkylenated ($C_6$-$C_{24}$)alkylamido ether carboxylic acids and salts thereof, such as those comprising from 2 to 15 alkylene oxide groups, ($C_6$-$C_{24}$)alkylpolyglycosidecarboxylic esters and salts thereof, and ($C_6$-$C_{24}$)acyl glutamates and salts thereof, and mixtures thereof, may be used.

In at least one further embodiment, polyoxyalkylenated ($C_6$-$C_{24}$)alkyl ether carboxylic acids and salts thereof, and polyoxyalkylenated ($C_6$-$C_{24}$)alkylamido ether carboxylic acids, such as those comprising from 2 to 15 alkylene oxide groups, and salts thereof, and mixtures thereof, are used.

The anionic surfactants of the polyoxyalkylenated carboxylic ether acid or salt type include, but are not limited to, those that correspond to formula (1) below:

$$R_1\text{—}(OC_2H_4)_n\text{—}OCH_2COOA \quad (1)$$

wherein:

$R_1$ is chosen from a linear or branched ($C_8$-$C_{22}$)alkyl or alkenyl radical or mixture of radicals, a ($C_8$-$C_9$)alkylphenyl radical, and a radical $R_2CONH\text{—}CH_2\text{—}CH_2\text{—}$, wherein R2 is chosen from a linear or branched ($C_{11}$-$C_{21}$)alkyl or alkenyl radical;

n is an integer or decimal number (average value) in a range from 2 to 24, for example from 2 to 10, the alkyl radical may comprise from 6 to 20 carbon atoms, for example from 8 to 18 carbon atoms; and A is chosen from H, ammonium, Na, K, Li, Mg, and monoethanolamine and triethanolamine residues. Mixtures of compounds of formula (1) may also be used, for example mixtures wherein the compounds of formula (1) possess different $R_1$ groups.

The oxyalkylenated ether carboxylic acids or salts thereof used in at least one embodiment according to the present disclosure are chosen from those of formula (1) wherein $R_1$ is chosen from ($C_{12}$-$C_{14}$)alkyls, cocoyl and oleyl radicals and mixtures thereof, and nonylphenyl and octylphenyl radicals; A is chosen from hydrogen and sodium atoms; and n is in a range from 2 to 20, for example from 2 to 10.

In at least one other embodiment, compounds of formula (1) are used wherein $R_1$ is a ($C_{12}$)alkyl radical, A is chosen from hydrogen and sodium atoms, and n is in a range from 2 to 10.

Non-limiting examples of the commercial products that may be used are the products sold by the company Chem Y under the names:

AKYPO® NP 70 ($R_1$=nonylphenyl, n=7, A=H);
AKYPO® NP 40 ($R_1$=nonylphenyl, n=4, A=H);
AKYPO® OP 40 ($R_1$=octylphenyl, n=4, A=H);
AKYPO® OP 80 ($R_1$=octylphenyl, n=8, A=H);
AKYPO® OP 190 ($R_1$=octylphenyl, n=19, A=H);
AKYPO® RLM 38 ($R_1$=($C_{12}$-$C_{14}$)alkyl, n=3.8, A=H);
AKYPO® RLM 38 NV ($R_1$=($C_{12}$-$C_{14}$)alkyl, n=4, A=Na);
AKYPO® RLM 45 ($R_1$=($C_{12}$-$C_{14}$)alkyl, n=4.5, A=H);
AKYPO® RLM 45 NV ($R_1$=($C_{12}$-$C_{14}$)alkyl, n=4.5, A=Na);
AKYPO® RLM 100 ($R_1$=($C_{12}$-$C_{14}$)alkyl, n=10, A=H);
AKYPO® RLM 100 NV ($R_1$=($C_{12}$-$C_{14}$)alkyl, n=10, A=Na);
AKYPO® RLM 130 ($R_1$=($C_{12}$-$C_{14}$)alkyl, n=13, A=H); and
AKYPO® RLM 160 NV ($R_1$=($C_{12}$-$C_{14}$)alkyl, n=16, A=Na);

or by the company Sandoz under the names:

SANDOPAN® DTC-Acid ($R_1$=($C_{13}$)alkyl, n=6, A=H);
SANDOPAN® DTC ($R_1$=($C_{13}$)alkyl, n=6, A=Na);
SANDOPAN® LS 24 ($R_1$=($C_{12}$-$C_{14}$)alkyl, n=12, A=Na); and
SANDOPAN® JA 36 ($R_1$=($C_{13}$)alkyl, n=18, A=H), and, in at least one embodiment, the products sold under the following names:

AKYPO® RLM 45;
AKYPO® RLM 100; and
AKYPO® RLM 38.

The carboxylic anionic surfactants other than the at least one anionic surfactant of (A) may be present in an amount ranging from 0.5% to 15% by weight, for example from 1% to 10% by weight, from 1.5% to 8% by weight, and from 2% to 5% by weight, relative to the total weight of the composition.

(C) Amphoteric and/or Zwitterionic Surfactants

The at least one amphoteric or zwitterionic surfactant may be, but are not limited to, aliphatic secondary or tertiary amine derivatives wherein the aliphatic radical is a linear or branched chain comprising from 8 to 22 carbon atoms and comprising at least one water-soluble anionic group (for example carboxylate, sulfonate, sulfate, phosphate or phosphonate); non-limiting mention may also be made of ($C_8$-$C_{20}$)alkylbetaines, sulfobetaines, ($C_8$-$C_{20}$)alkylamido($C_1$-$C_6$)alkylbetaines, and ($C_8$-$C_{20}$)alkylamido($C_1$-$C_6$)alkylsulfobetaines.

Among the amine derivatives, non-limiting mention may be made of the products as described in U.S. Pat. Nos. 2,528,378 and 2,781,354 and of the formula (2) and (3) below:

$$R_2\text{—}CONHCH_2CH_2\text{—}N(R_3)(R_4)(CH_2COO\text{—}) \quad (2)$$

wherein:

$R_2$—CO is chosen from a ($C_6$-$C_{24}$)acyl radical, for example, but not limited to, a radical present in hydrolyzed coconut oil, an octyl, decoyl or dodecanoyl radical, and mixtures thereof;

$R_3$ is a β-hydroxyethyl group; and
$R_4$ is a carboxymethyl group;
and $$R_{2'}\text{—}CONHCH_2CH_2\text{—}N(B)(C') \quad (3)$$

wherein:

B is —$CH_2CH_2OX'$, wherein X' is chosen from —$CH_2CH_2$—COOH and a hydrogen atom;

C' is —$(CH_2)_n$—Y' wherein z is an integer chosen from 1 and 2, and Y' is chosen from —COOH and —$CH_2$—CHOH—$SO_3H$; and $R_{2'}$—CO is a ($C_6$-$C_{24}$)acyl radical, for example, but not limited to, a radical present in hydrolyzed coconut oil or linseed oil, or an octyl, decoyl or dodecanoyl, stearoyl, isostearoyl or oleoyl radical, and mixtures thereof.

These compounds are classified in the CTFA dictionary, 5th edition, 1993, under the names disodium cocoamphodiacetate, disodium lauroamphodiacetate, disodium caprylamphodiacetate, disodium caryloamphodiacetate, disodium cocoamphodipropionate, disodium lauroamphodipropionate, disodium caprylamphodipropionate, disodium caryloamphodipropionate, lauroamphodipropionic acid, and cocoamphodipropionic acid.

A non-limiting example is disodium cocoamphodiacetate, sold under the trade name MIRANOL® C2M Concentrate by the company Rhodia Chimie.

According to the present disclosure, in at least one aspect, amphoteric surfactants belonging to the betaine group such as alkylbetaines, for example the cocoylbetaine sold under the name DEHYTON® AB 30 as an aqueous solution containing 30% AM by the company Henkel, or alkylamidobetaines, such as cocamidopropylbetaine, for example TEGOBETAINE® F50 sold by the company Goldschmidt, are used.

The at least one amphoteric or zwitterionic surfactant may be present in an amount ranging from 0.1% to 20% by weight, for example from 1% to 15% by weight, from 2% to 10% by weight and from 3% to 7% by weight, relative to the total weight of the composition.

(D) Alkylpolyglycoside Non Ionic Surfactants

The at least one alkylpolyglycoside nonionic surfactant of the present disclosure may be, in at least one aspect, represented by the following general formula (4):

$$R_1O\text{—}(R_2O)_t(G)_v \quad (4)$$

wherein

R$_1$ is chosen from a linear or branched alkyl and/or alkenyl radical comprising from 8 to 24 carbon atoms, and an alkylphenyl radical;

R$_2$ is an alkylene radical comprising from 2 to 4 carbon atoms;

G is a sugar unit comprising from 5 to 6 carbon atoms;

t is an integer in a range from 0 to 10, for example from 0 to 4; and v is an integer in a range from 1 to 15.

In at least one embodiment, the at least one alkylpolyglycoside according to the present disclosure is chosen from compounds of formula (4) wherein R$_1$ is chosen from a saturated or unsaturated, linear or branched alkyl radical comprising from 8 to 18 carbon atoms, t is an integer in a range from 0 to 3, for example 0, and G is chosen from glucose, fructose, and galactose, for example glucose. The degree of polymerization, i.e. the value of v in formula (4), may range from 1 to 15, for example from 1 to 4. The mean degree of polymerization is, in at least one embodiment, in a range from 1 to 2, for example from 1.1 to 1.5.

The glycoside bonds between the sugar units are of 1-6 or 1-4 type.

Compounds of formula (4) are, in at least one embodiment, chosen from the products sold by the company Cognis under the names PLANTAREN® (600 CS/U, 1200 and 2000) or PLANTACARE® (818, 1200 and 2000). In at least one other embodiment, compounds of formula (4) are chosen from the products sold by the company SEPPIC under the names TRITON® CG 110 (or ORAMIX® CG 110) and TRITON® CG 312 (or ORAMIX® NS 10), the products sold by the company BASF under the name LUTENSOL® GD 70, and the products sold by the company Chem Y under the name AG10 LK.

In at least one embodiment, the at least one alkylpolyglycoside nonionic surfactant used, for example, may be (C$_8$/C$_{1-6}$)alkyl polyglucoside-1,4 as an aqueous 53% solution sold by Cognis under the reference PLANTACARE® 818 UP.

The at least one alkylpolyglycoside nonionic surfactant can be present in an amount ranging from 0.1% to 20% by weight, for example from 1% to 15% by weight, from 2% to 10% by weight, and from 3% to 8% by weight, relative to the total weight of the composition.

The minimum amount of surfactant is the amount that is sufficient to give the final composition satisfactory latherability and/or detergent power, and excessive amounts of surfactants do not really afford any additional advantages.

Thus, according to the present disclosure, the total amount of surfactants may range from 4% to 50% by weight, for example from 6% to 35% by weight, and from 8% to 25% by weight, relative to the total weight of the final composition.

The sulfate, sulfonate or phosphate anionic surfactant/amphoteric surfactant weight ratio, in at least one aspect of the present disclosure, is in a range from 0.1 to 2, for example from 0.5 to 1 and from 0.7 to 0.8.

In at least one further aspect of the present disclosure, the sulfate, sulfonate or phosphate anionic surfactant/carboxylic anionic surfactant weight ratio is in a range from 0.1 to 10, for example from 0.5 to 5 and from 1 to 3.

The carboxylic anionic surfactant/amphoteric surfactant weight ratio, in at least one aspect of the present disclosure, is in a range from 0.1 to 10, for example from 0.2 to 5 and from 0.3 to 2.

The cosmetic composition according to the present disclosure comprises at least one cationic polymer with a cationic charge density of greater than or equal to 4 milliequivalents per gram (meq./g), for example greater than or equal to 5 meq./g, such as in a range from 5 to 20 meq./g and from 5.5 to 10 meq./g.

The cationic charge density of a polymer corresponds to the number of moles of cationic charges per unit of mass of polymer under conditions wherein this polymer is totally ionized. It may be determined by calculation if the structure of the polymer is known, i.e. the structure of the monomers constituting the polymer and their molar or weight proportion. It may also be determined experimentally via the Kjeldahl method, generally at pH of about 7 at room temperature.

The at least one cationic polymer with a cationic charge density of greater than or equal to 4 meq./g that may be used in accordance with the present disclosure may be chosen from all those already known as improving the cosmetic properties of the hair treated with compositions, for example those described in patent application EP-A-0 337 354 and in French patent applications FR-A-2 270 846, 2 383 660, 2 598 611, 2 470 596 and 2 519 863.

For the purposes of the present disclosure, the term "cationic polymer" is any polymer comprising at least one cationic group that may be ionized into cationic group.

The at least one cationic polymer may be chosen from those containing units comprising primary, secondary, tertiary, and/or quaternary amine groups that either may form part of the main polymer chain or may be borne by a side substituent directly attached thereto.

The at least one cationic polymer used may have a number-average molecular mass in a range from 500 to $5 \times 10^6$, for example in range from $10^3$ to $3 \times 10^6$.

In at least one aspect of the present disclosure, the at least one cationic polymer is chosen from polymers of the polyamine, polyamino amide, and polyquaternary ammonium type. These are known products.

Among these polymers, non-limiting mention may be made of:

(1) homopolymers or copolymers derived from acrylic or methacrylic esters or amides and comprising at least one of the units of the following formulae:

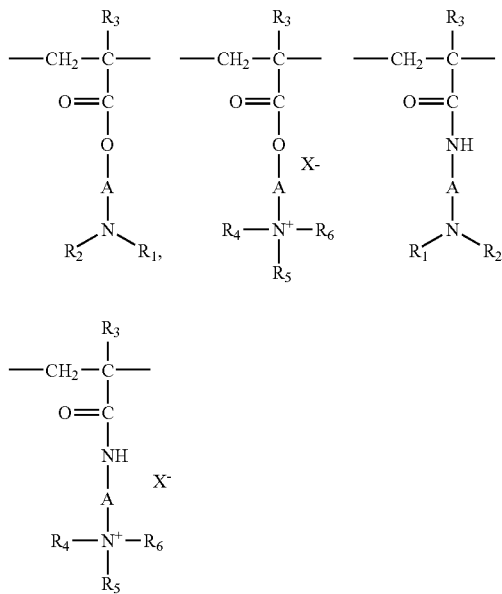

wherein:

$R_3$, which may be identical or different, is chosen from a hydrogen atom and a $CH_3$ radical;

A, which may be identical or different, is chosen from linear or branched alkyl groups comprising from 1 to 6 carbon atoms, for example from 2 to 3 carbon atoms, and hydroxyalkyl groups comprising from 1 to 4 carbon atoms;

$R_4$, $R_5$ and $R_6$, which may be identical or different, are chosen from alkyl groups comprising from 1 to 18 carbon atoms and a benzyl radical, and in at least one embodiment, $R_4$, $R_5$ and $R_6$, which may be identical or different, are chosen from alkyl groups comprising from 1 to 6 carbon atoms;

$R_1$ and $R_2$, which may be identical or different, are chosen from hydrogen and alkyl groups comprising from 1 to 6 carbon atoms, for example methyl or ethyl; and $X^-$ is chosen from anions derived from a mineral or organic acid, such as a methosulfate anion, and halides, such as chloride or bromide.

The copolymers of family (1) may also comprise at least one unit derived from comonomers that may be chosen from the family of acrylamides, methacrylamides, diacetone acrylamides, acrylamides, and methacrylamides substituted on the nitrogen with lower ($C_1$-$C_4$)alkyls, acrylic or methacrylic acids or esters thereof, vinyllactams, such as vinylpyrrolidone or vinylcaprolactam, and vinyl esters.

Thus, among these copolymers of family (1), non-limiting mention may be made of:

copolymers of acrylamide and of dimethylaminoethyl methacrylate quaternized with dimethyl sulfate or with a dimethyl halide, the copolymers of acrylamide and of methacryloyloxyethyltrimethylammonium chloride described, for example, in patent application EP-A-080 976, the copolymer of acrylamide and of methacryloyloxyethyltrimethylammonium methosulfate, quaternized or nonquaternized vinylpyrrolidone/dialkylaminoalkyl acrylate or methacrylate copolymers, such as those described in detail in French patents 2 077 143 and 2 393 573, dimethylaminoethyl methacrylate/vinylcaprolactam/vinylpyrrolidone terpolymers, vinylpyrrolidone/methacrylamidopropyldimethylamine copolymers, and and quaternized vinylpyrrolidone/dimethylaminopropylmethacrylamide copolymers.

(2) cationic polysaccharides, for example non-limiting mention may be made of cationic celluloses and cationic galactomannan gums. In at least one embodiment, the cationic polysaccharides are cellulose ether derivatives comprising quaternary ammonium groups, cationic cellulose copolymers or cellulose derivatives grafted with a water-soluble quaternary ammonium monomer and cationic galactomannan gums.

(3) polymers comprising piperazinyl units and divalent alkylene or hydroxyalkylene radicals comprising straight or branched chains, optionally interrupted by oxygen, sulfur or nitrogen atoms or by aromatic or heterocyclic rings, and also the oxidation and/or quaternization products of these polymers.

(4) water-soluble polyamino amides prepared, as non-limiting example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyidiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain at least one tertiary amine function, they can be quaternized.

(5) polyaminoamide derivatives resulting from the condensation of polyalkylene polyamines with polycarboxylic acids followed by alkylation with difunctional agents. Non-limiting mention may be made, for example, of adipic acid/dialkylamino-hydroxyalkyldialkylenetriamine polymers wherein the alkyl radical comprises from 1 to 4 carbon atoms, such as methyl, ethyl or propyl. Among these derivatives, non-limiting mention may be made of the adipic acid/dimethylaminohydroxypropyl/diethylenetriamine polymers.

(6) polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms.

(7) cyclopolymers of alkyldiallylamine or of dialkyldiallylammonium, such as the homopolymers or copolymers comprising, as main constituent of the chain, units corresponding to formula (5) or (5'):

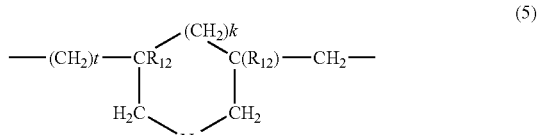

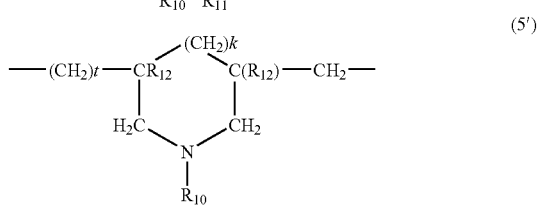

wherein k and t are equal to 0 or 1, the sum k+t being equal to 1; $R_{12}$ is chosen from a hydrogen atom and a methyl radical; $R_{10}$ and $R_{11}$, which may be identical or different, are chosen from alkyl groups comprising from 1 to 6 carbon atoms, hydroxyalkyl groups wherein the alkyl group, for example, comprises from 1 to 5 carbon atoms, and lower ($C_1$-$C_4$)amidoalkyl groups, or $R_{10}$ and $R_{11}$, together with the nitrogen atom to which they are attached, are chosen from heterocyclic groups such as piperidyl or morpholinyl; and $Y^-$ is an anion such as bromide, chloride, acetate, borate, citrate, tartrate, bisulfate, bisulfite, sulfate or phosphate. Such polymers are described, for example, in French patent 2 080 759 and in its Certificate of Addition 2 190 406.

In at least one embodiment, $R_{10}$ and $R_{11}$, which may be identical or different, are chosen from alkyl groups comprising from 1 to 4 carbon atoms.

Among the polymers defined above, non-limiting mention may be made, for example, of the dimethyldiallylammonium chloride homopolymers sold under the name MERQUAT® 100 by the company Nalco (and its homologs of low weight-average molar mass) and copolymers of diallyldimethylammonium chloride and of acrylamide.

(8) quaternary diammonium polymers containing repeating units corresponding to the formula (6):

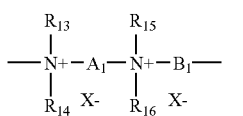
(6)

wherein:

$R_{13}$, $R_{14}$, $R_{15}$ and $R_{16}$, which may be identical or different, are chosen from aliphatic, alicyclic or arylaliphatic radicals comprising from 1 to 20 carbon atoms, and lower hydroxyalkylaliphatic radicals such as hydroxyethyl, or $R_{13}$, $R_{14}$, $R_{15}$ and $R_{16}$, together or separately, constitute, with the nitrogen atoms to which they are attached, heterocycles optionally comprising a second heteroatom other than nitrogen, or $R_{13}$, $R_{14}$, $R_{15}$ and $R_{16}$ are chosen from a linear or branched ($C_1$-$C_6$)alkyl radical substituted with a nitrile, ester, acyl, or amide group, and a group —CO—O—$R_{17}$-D or —CO—NH—$R_{17}$-D wherein $R_{17}$ is an alkylene and D is a quaternary ammonium group;

$A_1$ and $B_1$ are chosen from polymethylene groups comprising from 2 to 20 carbon atoms, wherein the polymethylene groups may be linear or branched, saturated or unsaturated, and wherein the polymethylene groups may comprise, linked to or intercalated in the main chain, at least one aromatic ring, at least one oxygen or sulfur atom, or sulfoxide, sulfone, disulfide, amino, alkylamino, hydroxyl, quaternary ammonium, ureido, amide or ester groups, and $X^-$ is an anion derived from a mineral or organic acid;

or $A_1$, $R_{13}$ and $R_{15}$ can form, with the two nitrogen atoms to which they are attached, a piperazine ring; in addition, if $A_1$ is chosen from a linear or branched, saturated or unsaturated alkylene or hydroxyalkylene radical, $B_1$ is chosen from polymethylene groups comprising from 2 to 20 carbon atoms, wherein the polymethylene groups may be linear or branched, saturated or unsaturated, and wherein the polymethylene groups may comprise, linked to or intercalated in the main chain, at least one aromatic ring, at least one oxygen or sulfur atom, sulfoxide, sulfone, disulfide, amino, alkylamino, hydroxyl, quaternary ammonium, ureido, amide or ester groups, and a group $(CH_2)_n$—CO-D-OC—$(CH_2)_n$—;

wherein D is chosen from:

a) a glycol residue of formula: —O-Z-O—, wherein Z is chosen from a linear or branched hydrocarbon-based radical, and a group corresponding to one of the following formulae:

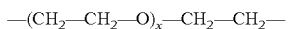

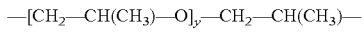

wherein x and y are integers ranging from 1 to 4, which is a defined and unique degree of polymerization or an average degree of polymerization;

b) a bis-secondary diamine residue, such as a piperazine derivative;

c) a bis-primary diamine residue of formula: —NH—Y—NH—, wherein Y is chosen from a linear or branched hydrocarbon-based-radical, and the divalent radical

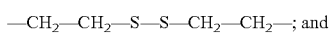

d) a ureylene group of formula: —NH—CO—NH—; and n is an integer ranging from 1 to 20, for example from 1 to 10.

In at least one embodiment, $X^-$ is an anion such as chloride or bromide.

These polymers can have a number-average molar mass in a range from 1,000 to 100,000.

In at least one embodiment, polymers that consist of repeating units corresponding to formula (a) are used:

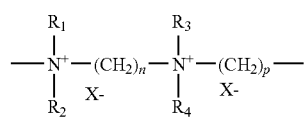
(a)

wherein $R_1$, $R_2$, $R_3$ and $R_4$, which may be identical or different, are chosen from alkyl and hydroxyalkyl radicals comprising from 1 to 4 carbon atoms, n and p are integers ranging from 2 to 20, and $X^-$ is an anion derived from a mineral or organic acid.

In at least one embodiment, $R_1$, $R_2$, $R_3$ and $R_4$ are chosen from a methyl radical and n=3, p=6 and X=Cl. Such a polymer is known as Hexadimethrine chloride according to the INCI (CTFA) nomenclature.

(9) polyquaternary ammonium polymers comprised of units of formula (7):

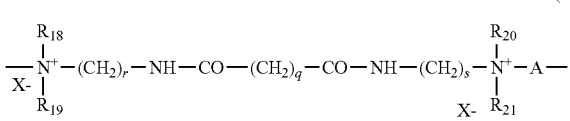
(7)

wherein:

$R_{18}$, $R_{19}$, $R_{20}$ and $R_{21}$, which may be identical or different, are chosen from a hydrogen atom, and methyl, ethyl, propyl, β-hydroxyethyl, β-hydroxypropyl and —$CH_2CH_2$ ($OCH_2CH_2$)$_p$OH radicals, wherein p is equal to 0 or to an integer ranging from 1 to 6, with the proviso that $R_{18}$, $R_{19}$, $R_{20}$ and $R_{21}$ do not simultaneously represent a hydrogen atom, r and s, which may be identical or different, are integers ranging from 1 to 6, q is an integer ranging from 1 to 34, $X^-$ is an anion such as a halide, A is chosen from a dihalide radical and —$CH_2$—$CH_2$—O—$CH_2$—$CH_2$—. In at least one embodiment, A is —$CH_2$—$CH_2$—O—$CH_2$—$CH_2$—.

Non-limiting examples of such compounds are described in patent application EP-A-122 324.

Non-limiting examples include the products MIRAPOL® A15, MIRAPOL® AD1, MIRAPOL® AZ1 and MIRAPOL® 175 sold by the company Miranol.

(10) quaternary polymers of vinyllactam (vinylpyrrolidone and/or vinylcaprolactam) and of vinylimidazole.

(11) crosslinked polymers of methacryloyloxy(C1-C4) alkyltri(C1-C4)alkyl-ammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for example methylenebisacrylamide.

Other cationic polymers that can be used in the context of the disclosure are cationic proteins or cationic protein hydrolysates, polyalkyleneimines, for example non-limiting mention may be made of polyethyleneimines, polymers containing vinylpyridine or vinylpyridinium units, condensates of polyamines and of epichlorohydrin, quaternary polyureylenes and chitin derivatives.

In at least one aspect of the present disclosure, those families of cationic polymers (1), (7), (8), (9) and (10) are used.

In at least one embodiment, the cationic cyclopolymers used are chosen from the dimethyldiallylammonium chloride homopolymers sold under the name MERQUAT® 100 by the company Nalco, diquaternary ammonium polymers and polyethyleneimines, and mixtures thereof.

The at least one cationic polymer with a cationic density of greater than or equal to 4 meq./g may be present in an amount ranging from 0.01% to 20% by weight, for example from 0.05% to 10% by weight, from 0.1% to 5% by weight, and from 0.2% to 2% by weight, relative to the total weight of the composition.

The at least one agent that is beneficial to keratin materials other than the at least one cationic polymer of (E) may be chosen from:
(1) hydrolyzed or nonhydrolyzed, modified or unmodified saccharides, oligosaccharides and polysaccharides,
(2) hydrolyzed or nonhydrolyzed, modified or unmodified amino acids, oligopeptides, peptides and proteins,
(3) branched or unbranched fatty acids and alcohols,
(4) animal, plant and mineral waxes,
(5) ceramides and pseudoceramides,
(6) hydroxylated organic acids,
(7) UV-screening agents,
(8) antioxidants and free-radical scavengers,
(9) chelating agents,
(10) antidandruff agents,
(11) seborrhea regulators,
(12) calmatives,
(13) cationic surfactants,
(14) organomodified and non-organomodified silicones,
(15) mineral, plant and animal oils,
(16) polyisobutenes and poly($\alpha$-olefins),
(17) fatty esters, for example those comprising from 15 to 50 carbon atoms,
(18) soluble and dispersed anionic polymers, and
(19) soluble and dispersed nonionic polymers, and mixtures thereof.

The composition according to the present disclosure may comprise one or more identical or different, hydrolyzed or nonhydrolyzed, modified or unmodified saccharides, oligosaccharides or polysaccharides. Non-limiting examples of the compounds of this type that may be used in the present disclosure may be chosen from those described in Kirk-Othmer's "Encyclopedia of Chemical Technology", Third Edition, 1982, volume 3, pp. 896-900 and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc., the content of these three publications being incorporated by reference in their entirety in the present disclosure.

Non-limiting examples of modified or unmodified, optionally hydrolyzed saccharides, oligosaccharides and polysaccharides that may be used in the disclosure, include those made of glucans, modified or unmodified starches (such as those derived from cereals, for instance wheat, corn or rice, from vegetables, for instance haricot beans, from tubers, for instance potato or cassava), other than the starch betainate as described above, amylose, amylopectin, glycogen, dextrans, β-glucans, celluloses and derivatives thereof (such as methylcelluloses, hydroxyalkylcelluloses, ethylhydroxyethylcelluloses or carboxymethylcelluloses), fructosans, inulin, levan, mannans, xylans, lignins, arabans, galactans, galacturonans, chitin, glucoronoxylans, arabinoxylans, xyloglucans, galactomannans, glucomannans, pectic acids and pectins, alginic acid and alginates, arabinogalactans, carrageenans, agars, glycosaminoglucans, gum arabics, gum tragacanths, ghatti gums, karaya gums, carob gums, guar gums and xanthan gums, and mixtures thereof.

The composition according to the present disclosure may comprise at least one hydrolyzed or nonhydrolyzed, modified or unmodified amino acid, oligopeptide, peptide or protein. Non-limiting examples of amino acids include cysteine, lysine, alanine, N-phenylalanine, arginine, glycine and leucine, and mixtures thereof. As modified or unmodified, optionally hydrolyzed oligopeptides, peptides and proteins that may be used according to the disclosure, non-limiting mention may be made of modified or unmodified wool or silk protein hydrolysates, and plant proteins such as wheat proteins.

The composition according to the disclosure may comprise at least one branched or unbranched fatty acid or alcohol. Among the fatty acids that are suitable for use in the present disclosure, non-limiting mention may be made of ($C_8$-$C_{30}$) carboxylic acids, such as palmitic acid, oleic acid, linoleic acid, myristic acid, stearic acid and lauric acid, and mixtures thereof. Non-limiting examples of the fatty alcohols that may be used in the present disclosure include ($C_8$-$C_{30}$) alcohols, such as palmityl alcohol, oleyl alcohol, linoleyl alcohol, myristyl alcohol, stearyl alcohol and lauryl alcohol, and mixtures thereof.

The composition according to the disclosure may comprise at least one animal, plant or mineral wax.

For the purposes of the present disclosure, a wax is a lipophilic compound that is solid at room temperature (about 25° C.), with a reversible solid/liquid change of state, having a melting point of greater than about 40° C. and which may be up to 200° C., and having an anisotropic crystal organization in the solid state. In general, the size of the wax crystals is such that crystals scatter and/or diffuse light, giving the composition comprising them a more or less opaque, cloudy appearance. By raising the wax to its melting point, it is possible to make it miscible with oils and to form a microscopically homogeneous mixture, but on returning the temperature of the mixture to room temperature, a microscopically and macroscopically detectable recrystallization of the wax in the oils of the mixture is obtained (opalescence).

As waxes that may be used in the present disclosure, non-limiting mention may be made of waxes of animal origin, such as beeswax, spermaceti, lanolin wax and lanolin derivatives; plant waxes, such as carnauba wax, candelilla wax, ouricury wax, Japan wax, cocoa butter, cork fiber wax or sugar cane wax; mineral waxes, such as paraffin wax, petroleum jelly wax, lignite wax, microcrystalline waxes or ozokerites; and mixtures thereof.

The composition according to the disclosure may comprise at least one ceramide and/or pseudoceramide. Non-limiting mention may be made of the ceramides of categories I, II, III and V according to the Dawning classification, and mixtures thereof, for example N-oleyldehydrosphingosine.

The composition according to the disclosure may comprise at least one hydroxylated organic acid chosen from those that are well known and used in the art. Non-limiting mention may be made of citric acid, lactic acid, tartaric acid and malic acid, and mixtures thereof.

The composition according to the disclosure may comprise at least one UV-A-active and/or UV-B-active sunscreens that are well known to those skilled in the art. Non-limiting mention may be made of dibenzoylmethane derivatives such as 4-methyldibenzoylmethane, 4-isopropyldibenzoylmethane, 4-tert-butyldibenzoylmethane, 2,4-dimethyldibenzoylmethane, 4-tert-butyl-4'-diisopropyldibenzoylmethane, p-aminobenzoic acid and its esters such as 2-ethylhexyl p-dimethylaminobenzoate and N-propoxylated ethyl p-aminobenzoate, salicylates such as triethanolamine salicylate, cinnamic acid esters such as 2-ethylhexyl 4-methoxycinnamate, methyl diisopropylcinnamate, menthyl anthranilate, benzotriazole derivatives, triazine derivatives, β,β'-diphenylacrylate derivatives such as 2-ethylhexyl 2-cyano-3,3-diphenylacrylate and ethyl 2-cyano-3,3-diphenylacrylate, 2-phenylbenzimidazole-5-sulfonic acid and its salts, benzophenone derivatives, benzylidenecamphor derivatives, silicone screening agents, and mixtures thereof.

Non-limiting examples of antioxidants and free-radical scavengers that may be used in the present disclosure include ascorbic acid, ascorbyl compounds such as ascorbyl dipalmitate, t-butylhydroquinone, polyphenols such as phloroglucinol, sodium sulfite, erythorbic acid and flavonoids, and mixtures thereof.

The composition according to the disclosure may comprise at least one chelating agent. Non-limiting examples include EDTA (ethylenediaminetetraacetic acid) and salts thereof such as disodium EDTA and dipotassium EDTA, phosphate compounds such as sodium metaphosphate, sodium hexametaphosphate and tetrapotassium pyrophosphate, and phosphonic acids and salts thereof, such as ethylenediaminetetramethylenephosphonic acid salts, and mixtures thereof.

The composition according to the disclosure may comprise at least one antidandruff agent, non-limiting examples of which include:

benzethonium chloride, benzalkonium chloride, chlorhexidine, chloramine T, chloramine B, 1,3-dibromo-5,5-dimethylhydantoin, 1,3-dichloro-5,5-dimethylhydantoin, 3-bromo-1-chloro-5,5-dimethylhydantoin and N-chlorosuccinimide;

1-hydroxy-2-pyridone derivatives, such as 1-hydroxy-4-methyl-2-pyridone, 1-hydroxy-6-methyl-2-pyridone and 1-hydroxy-4,6-dimethyl-2-pyridone;

trihalocarbamides;

triclosan;

azole compounds, such as climbazole, ketoconazole, clotrimazole, econazole, isoconazole and miconazole b;

antifungal polymers, such as amphotericin B and nystatin;

selenium sulfides;

sulfur in its various forms, cadmium sulfide, allantoin, coal tar and wood tar and derivatives thereof, cade oil, undecylenic acid, fumaric acid and allylamines such as terbinafine; and a mixture of these antidandruff agents.

The antidandruff agents may also be used in the form of the addition salts thereof with physiologically acceptable acids, non-limiting examples include in the form of the sulfuric acid, nitric acid, thiocyanic acid, hydrochloric acid, hydrobromic acid, hydriodic acid, phosphoric acid, acetic acid, benzoic acid, glycolic acid, aceturic acid, succinic acid, nicotinic acid, tartaric acid, maleic acid, palmitic acid, methanesulfonic acid, propanoic acid, 2-oxopropanoic acid, propanedioic acid, 2-hydroxy-1,4-butanedioic acid, 3-phenyl-2-propenoic acid, α-hydroxybenzeneacetic acid, ethanesulfonic acid, 2-hydroxyethanesulfonic acid, 4-methylbenzenesulfonic acid, 4-amino-2-hydroxybenzoic acid, 2-phenoxybenzoic acid, 2-acetyloxybenzoic acid, picric acid, lactic acid, citric acid, malic acid, oxalic acid, and amino acid salts.

The antidandruff agents mentioned above may also, where appropriate, be used in the form of the addition salts thereof with physiologically acceptable organic or mineral bases. Non-limiting examples of organic bases include low molecular weight alkanolamines such as ethanolamine, diethanolamine, N-ethylethanolamine, triethanol-amine, diethylaminoethanol and 2-amino-2-methylpropanedione; nonvolatile bases such as ethylenediamine, hexamethylenediamine, cyclohexylamine, benzylamine and N-methylpiperazine; quaternary ammonium hydroxides, for example trimethylbenzyl hydroxide; guanidine and its derivatives, for example its alkyl derivatives. Non-limiting examples of mineral bases include the alkali metal salts, for instance the sodium or potassium salts; the ammonium salts; the alkaline-earth metal salts, for instance the magnesium or calcium salts; the salts of cationic di-, tri- or tetravalent metals, for instance the zinc, aluminum and zirconium salts. In at least one embodiment, the antidandruff agent is chosen from alkanolamines, ethylenediamine and mineral bases such as the alkali metal salts.

The composition according to the disclosure may comprise at least one seborrhea regulator, such as, but not limited to, succinylchitosan and poly-β-alanine, and mixtures thereof.

The composition according to the disclosure may comprise at least one calmative, such as, but not limited to, azulene and glycyrrhetinic acid, and mixtures thereof.

The composition according to the disclosure may comprise at least one cationic surfactant that is well known, such as, but not limited to, optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The silicones that may be used in accordance with the disclosure may be soluble or insoluble in the composition, and they may be, but are not limited to, polyorgano-siloxanes that are insoluble in the composition of the disclosure. They may be in the form of oils, waxes, resins or gums.

Non-limiting examples of the organopolysiloxanes are defined in greater detail in Walter Noll's "Chemistry and Technology of Silicones" (1968) Academic Press. They can be volatile or nonvolatile.

When they are volatile, the silicones are, in at least one aspect of the disclosure, chosen from those having a boiling point in a range from 60° C. to 260° C., and for example from:

(i) cyclic silicones comprising from 3 to 7 and for example from 4 to 5 silicon atoms. These are, for example, but not limited to, octamethylcyclotetrasiloxane sold under the name Volatile Silicone 7207 by Union Carbide or SILBIONE® 70045 V 2 by Rhodia, decamethylcyclopentasiloxane sold under the name Volatile Silicone 7158 by Union Carbide, and SILBIONE® 70045 V 5 by Rhodia, and mixtures thereof.

Non-limiting mention may also be made of cyclocopolymers of the dimethylsiloxane/methylalkylsiloxane type, such as Volatile Silicone FZ 3109 sold by the company Union Carbide, having the general chemical structure:

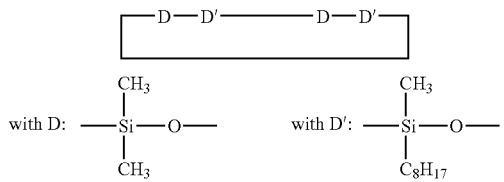

Non-limiting mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones comprising from 2 to 9 silicon atoms and having a viscosity of less than or equal to $5 \times 10^{-6}$ m$^2$/s at 25° C. A non-limiting example is decamethyltetrasiloxane sold under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Additional non-limiting examples of the nonvolatile silicones that may be mentioned include polyalkylsiloxanes, polyarylsiloxanes, polyalkylarylsiloxanes, silicone gums and resins, polyorganosiloxanes modified with organofunctional groups, and also mixtures thereof.

The organomodified silicones that can be used in accordance with the disclosure are silicones as defined above and comprising in their structure at least one organofunctional group attached via a hydrocarbon-based group.

Among the organomodified silicones, non-limiting mention may be made of polyorganosiloxanes comprising:
  polyethyleneoxy and/or polypropyleneoxy groups optionally comprising ($C_6$-$C_{24}$)alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;
  substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, ($C_1$-$C_4$)aminoalkyl groups;
  thiol groups, such as the products sold under the names GP 72 A and GP 71 from Genesee;
  alkoxylated groups, such as the product sold under the name Silicone Copolymer F-755 by SWS Silicones and ABIL WAX® 2428, 2434 and 2440 by the company Goldschmidt;
  hydroxylated groups, such as the polyorganosiloxanes comprising a hydroxyalkyl function, described in French patent application FR-A-85/16334;
  acyloxyalkyl groups, such as the polyorganosiloxanes described in U.S. Pat. No. 4,957,732;
  anionic groups of the carboxylic acid type, such as in the products described in patent EP 186 507 from the company Chisso Corporation, or of the alkylcarboxylic type, such as those present in the product X-22-3701E from the company Shin-Etsu; 2-hydroxyalkyl sulfonate; 2-hydroxyalkyl thiosulfate, such as the products sold by the company Goldschmidt under the names ABIL® S201 and ABIL® S255; and
  hydroxyacylamino groups, such as the polyorganosiloxanes described in patent application EP 342 834. Non-limiting mention may be made, for example, of the product Q2-8413 from the company Dow Corning.

The composition according to the disclosure may comprise at least one mineral, plant or animal oil. Oils of plant origin, for example, include, but are not limited to, sweet almond oil, avocado oil, castor oil, olive oil, jojoba oil, sunflower oil, wheatgerm oil, sesame seed oil, groundnut oil, grapeseed oil, soybean oil, rapeseed oil, safflower oil, coconut oil, corn oil, hazelnut oil, shea butter, palm oil, apricot kernel oil and beauty-leaf oil; oils of animal origin include, but are not limited to, perhydrosqualene; oils of mineral origin, for example, include but are not limited to, liquid paraffin and liquid petroleum jelly; and mixtures thereof.

The composition according to the disclosure may comprise at least one polyisobutene or poly(α-olefin), chosen from those that are well known in the art.

The composition according to the disclosure may comprise at least one ester. Non-limiting examples of esters include fatty acid esters, for example comprising from 8 to 22 carbon atoms, for instance isopropyl myristate, isopropyl palmitate, 2-ethylhexyl palmitate, purcellin oil (stearyl octanoate), isononyl isononanoate, isostearyl isononanoate and isopropyl lanolate, and mixtures thereof. Non-limiting mention may also be made of fatty alkyl esters, for example comprising from 8 to 22 carbon atoms.

The composition according to the disclosure may comprise at least one soluble or dispersed anionic polymers that are well known. The anionic polymers that may be used in the present disclosure include, but are not limited to, polymers comprising groups derived from carboxylic acids, sulfonic acids or phosphoric acids, and having a weight-average molecular mass in a range from 500 to 5,000,000.

The carboxylic groups may be provided by unsaturated monocarboxylic or dicarboxylic acid monomers such as those corresponding to formula (8):

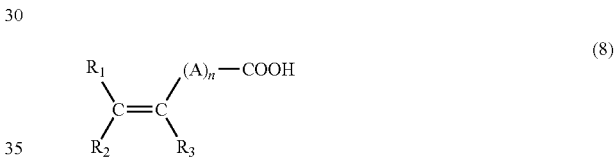

wherein n is an integer ranging from 0 to 10, A is a methylene group, optionally connected to the carbon atom of the unsaturated group or to the neighboring methylene group when n is greater than 1 via a heteroatom such as oxygen or sulfur, $R_1$ is chosen from a hydrogen atom, phenyl groups, and benzyl groups, $R_2$ is chosen from a hydrogen atom, lower alkyl groups, and carboxyl groups, and $R_3$ is chosen from a hydrogen atom, lower alkyl groups, a —$CH_2$—COOH group, phenyl groups, and benzyl groups.

In formula (8) above, a lower alkyl group, in at least one embodiment, comprises from 1 to 4 carbon atoms, for example methyl and ethyl groups.

Non-limiting examples of the anionic polymers containing carboxylic groups that are according to the disclosure include:

A) homo- or copolymers of acrylic or methacrylic acid or salts thereof, for example the products sold under the names VERSICOL® E or K by the company Allied Colloid, ULTRAHOLD® by the company BASF, the copolymers of acrylic acid and acrylamide sold in the form of their sodium salt under the names RETEN® 421, 423 or 425 by the company Hercules, and the sodium salts of polyhydroxycarboxylic acids;

B) copolymers of acrylic or methacrylic acids with a monoethylenic monomer such as ethylene, styrene, vinyl esters and acrylic or methacrylic acid esters, optionally grafted onto a polyalkylene glycol such as polyethylene glycol and optionally crosslinked. Such polymers are described, for example, in French patent 1 222 944 and German patent application No. 2 330 956. Non-limiting mention may be made of copolymers whose chain comprises an optionally N-alkylated and/or hydroxyalkylated acrylamide unit, such as those described, for example, in the Luxembourg patent applications 75370 and 75371 or sold under the name QUADRAMER® by the company American Cyanamid. Non-limiting mention may also be made of copolymers of acrylic acid and of ($C_1$-$C_4$)alkyl methacrylate and the copolymer of methacrylic acid and of ethyl acrylate sold under the name LUVIMER® MAEX by the company BASF;

C) copolymers derived from crotonic acid, such as those whose chain comprises vinyl acetate or propionate units and optionally other monomers such as allylic or methallylic esters, vinyl ether or vinyl ester of a saturated, linear or branched carboxylic acid comprising a long hydrocarbon-based chain such as those comprising at least 5 carbon atoms, it being possible for these polymers to be grafted and crosslinked, or alternatively a vinyl, allylic or methallylic ester of an α- or β-cyclic carboxylic acid. Such polymers are described, inter alia, in French patents 1 222 944, 1 580 545, 2 265 782, 2 265 781, 1 564 110 and 2 439 798. Commercial products falling within this category are the resins 28-29-30, 26-13-14 and 28-13-10 sold by the company National Starch;

D) polymers derived from maleic, fumaric or itaconic acids or anhydrides with vinyl esters, vinyl ethers, vinyl halides, phenylvinyl derivatives or acrylic acid and its esters; these polymers may be esterified. Such polymers are described, for example, in U.S. Pat. Nos. 2,047,398, 2,723,248, and 2,102,113 and GB patent 839 805, and, for example, those sold under the names GANTREZ® AN or ES by the company ISP. Polymers also falling within this category are the copolymers of maleic, citraconic or itaconic anhydrides and of an allylic or methallylic ester optionally comprising an acrylamide or methacrylamide group, an α-olefin, acrylic or methacrylic esters, acrylic or methacrylic acid or vinylpyrrolidone in their chain, the anhydride functions being monoesterified or monoamidated. These polymers are described, for example, in French patents 2 350 384 and 2 357 241 by the Applicant;

E) polyacrylamides comprising carboxylate groups.

The polymers comprising sulfonic groups are polymers comprising vinylsulfonic, styrenesulfonic, naphthalenesulfonic or acrylamidoalkylsulfonic units. These polymers can be chosen, for example, from:

polyvinylsulfonic acid salts with a molecular weight in a range from 1,000 to 100,000, and also copolymers with an unsaturated comonomer such as acrylic or methacrylic acids and esters thereof, and also acrylamide or derivatives thereof, vinyl ethers and vinylpyrrolidone;

polystyrenesulfonic acid salts, the sodium salts having a molecular weight in a range from 500,000 to 100,000, sold, respectively, under the names FLEXAN® 500 and FLEXAN® 130 by National Starch. These compounds are described in patent FR 2 198 719; and polyacrylamidesulfonic acid salts such as those mentioned in U.S. Pat. No. 4,128,631 and, for example, polyacrylamidoethylpropanesulfonic acid sold under the name COSMEDIA POLYMER® HSP 1180 by Henkel.

According to the disclosure, the anionic polymers are, in at least one embodiment, chosen from acrylic acid copolymers such as the acrylic acid/ethyl acrylate/N-tert-butylacrylamide terpolymer sold under the name ULTRAHOLD STRON® by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acids with vinyl esters, vinyl ethers, vinyl halides, phenylvinyl derivatives or acrylic acid and esters thereof, such as the methyl vinyl ether/monoesterified maleic anhydride copolymer sold under the name GANTREZ® ES 425 by the company ISP, the copolymers of methacrylic acid and of methyl methacrylate sold under the name EUDRAGIT® L by the company Rohm Pharma, the copolymer of methacrylic acid and of ethyl acrylate sold under the name LUVIMER® MAEX by the company BASF, the vinyl acetate/crotonic acid copolymer sold under the name LUVISET® CA 66 by the company BASF and the vinyl acetate/crotonic acid/polyethylene glycol terpolymer sold under the name ARISTOFLEX® A by the company BASF.

The anionic polymers, in at least one embodiment, are chosen from the methyl vinyl ether/monoesterified maleic anhydride copolymer sold under the name GANTREZ® ES 425 by the company ISP, the copolymers of methacrylic acid and of methyl methacrylate sold under the name EUDRAGIT® L by the company Rohm Pharma, the copolymer of methacrylic acid and of ethyl acrylate sold under the name LUVIMER® MAEX or MAE by the company BASF, and the vinylpyrrolidone/acrylic acid/lauryl methacrylate terpolymers sold under the name ACRYLIDONE® LM by the company ISP.

According to the disclosure, the anionic polymers may also be used in the form of a latex or pseudolatex, i.e. in the form of an aqueous dispersion of insoluble polymer particles.

The composition according to the disclosure may comprise at least one soluble or dispersed nonionic polymer. As nonionic polymers that may be used according to the present disclosure, non-limiting mention may be made of:

vinylpyrrolidone homopolymers;

copolymers of vinylpyrrolidone and vinyl acetate;

polyalkyloxazolines such as the polyethyloxazolines sold by the company Dow Chemical under the names PEOX® 50 000, PEOX® 200 000 and PEOX® 500 000;

vinyl acetate homopolymers, such as the product sold under the name APPRETAN® EM by the company Hoechst, or the product sold under the name RHODOPAS® A 012 by the company Rhône-Poulenc;

copolymers of vinyl acetate and acrylic ester, such as the product sold under the name RHODOPAS® AD 310 by Rhône-Poulenc;

copolymers of vinyl acetate and ethylene, such as the product sold under the name APPRETAN® TV by the company Hoechst;

copolymers of vinyl acetate and maleic ester, for example of dibutyl maleate, such as the product sold under the name APPRETAN® MB Extra by the company Hoechst;

copolymers of polyethylene and maleic anhydride;

alkyl acrylate homopolymers and alkyl methacrylate homopolymers, such as the product sold under the name MICROPEARL® RQ 750 by the company Matsumoto or the product sold under the name LUHYDRAN® A 848 S by the company BASF;

acrylic ester copolymers, for example, copolymers of alkyl acrylates and alkyl methacrylates, such as the products sold by the company Rohm & Haas under the names PRIMAL® AC-261 K and EUDRAGIT® NE 30 D, by the company BASF under the names ACRONAL® 601, LUHYDRAN® LR 8833 or 8845, and by the company Hoechst under the names APPRETAN® N 9213 or N 921 2;

copolymers of acrylonitrile and a nonionic monomer chosen, for example, from butadiene and alkyl (meth)acrylates; mention may be made of the products sold under the names NIPOL® LX 531 8 by the company Nippon Zeon or those sold under the name CJ 0601 8 by the company Rohm & Haas;

polyurethanes, such as the products sold under the names ACRYSOL® RM 1020 or ACRYSOL® RM 2020 by the company Rohm & Haas, and the products URAFLEX® XP 401 UZ and URAFLEX® XP 402 UZ by the company DSM Resins;

copolymers of alkyl acetate and urethane, such as the product 8538-33 by the company National Starch;

polyamides, such as the product ESTAPOR® LO 11 sold by the company Rhone-Poulenc; and unmodified or chemically modified nonionic guar gums, such as the products sold under the name VIDOGUM® GH 175 by the company Unipectine and under the name JAGUAR® C by the company Meyhall.

The modified nonionic guar gums that can be used according to the disclosure are, in at least one embodiment, modified with ($C_1$-$C_6$)hydroxyalkyl groups. Non-limiting mention may be made, for example, of hydroxymethyl, hydroxyethyl, hydroxypropyl and hydroxybutyl groups. These guar gums are well known in the state of the art and can be prepared, for example, by reacting corresponding alkene oxides, such as propylene oxides, with guar gum so as to obtain a guar gum modified with hydroxypropyl groups. Such nonionic guar gums optionally modified with hydroxyalkyl groups are sold, for example, under the trade names JAGUAR® HP8, JAGUAR® HP60 and JAGUAR® HP120, JAGUAR® DC 293 and JAGUAR® HP 105 by the company Meyhall or under the name GALACTASOL® 4H4FD2 by the company Aqualon.

The alkyl groups of the nonionic polymers, in at least one embodiment, comprise from 1 to 6 carbon atoms.

The at least one beneficial agent may be used in the compositions in accordance with the disclosure in a concentration range from 0.001% from 20% by weight, for example from 0.005% to 15% by weight, from 0.01% to 12% by weight, from 0.1% to 5% by weight, relative to the total weight of the final composition.

The detergent compositions according to the disclosure have a final pH in a range from 3 to 8. This pH is, in at least one embodiment, from 4 to 7.5. The pH may be adjusted to the desired value conventionally by adding a base (organic or mineral) to the composition, for example sodium hydroxide, aqueous ammonia or a primary, secondary or tertiary (poly) amine, for instance monoethanolamine, diethanolamine, triethanolamine, isopropanolamine or 1,3-propanediamine, or alternatively by adding a mineral or organic acid, for example citric acid or hydrochloric acid.

The cosmetically acceptable aqueous medium may consist solely of water or of a mixture of water and of a cosmetically acceptable solvent, such as a ($C_1$-$C_4$) lower alcohol, for instance ethanol, isopropanol, tert-butanol or n-butanol; alkylene glycols, for instance propylene glycol, hexylene glycol or glycerol.

The composition according to the disclosure, for example comprises at least 30% by weight of water, such as from 50% to 90% by weight, and from 70% to 85% by weight, relative to the total weight of the composition.

The compositions in accordance with the disclosure may comprise, in addition to the combination defined above, viscosity regulators such as thickeners. Non-limiting mention may be made of scleroglucans, xanthan gums, fatty acid alkanolamides, alkyl ether carboxylic acid alkanolamides optionally oxyethylenated with up to 5 mol of ethylene oxide, such as the product sold under the name AMINOL® A15 by the company Chem Y, crosslinked polyacrylic acids and crosslinked acrylic acid/($C_{10}$-$C_{30}$)alkyl acrylate copolymers.

These viscosity regulators are used in the compositions according to the disclosure in proportions that may be up to 10% by weight, relative to the total weight of the composition.

The compositions in accordance with the disclosure may also comprise up to 5% of nacreous agents or opacifiers that are well known in the state of the art, for instance fatty alcohols, sodium palmitate or magnesium palmitate, sodium or magnesium stearate or hydroxystearate, fatty alcohols, fatty-chain acyl derivatives such as ethylene glycol or polyethylene glycol distearates, and fatty-chain ethers, for instance distearyl ether or 1-(hexadecyloxy)-2-octadecanol.

The compositions according to the disclosure may also comprise foam synergists such as ($C_{10}$-$C_{18}$) 1,2-alkanediols or ($C_{10}$-$C_{18}$) fatty alkanolamides derived from mono- or diethanolamine.

The compositions according to the disclosure may also comprise additives such as natural or synthetic, anionic, amphoteric, zwitterionic, nonionic or cationic, associative or nonassociative polymeric thickeners, nonpolymeric thickeners such as acids or electrolytes, nacreous agents, opacifiers, organic solvents, fragrances, dyes, mineral or organic particles, preserving agents and pH stabilizers.

A person skilled in the art will take care to select the optional additives and the amount thereof such that they do not harm the properties of the treatment compositions.

These additives are present in the composition according to the disclosure in an amount ranging from 0 to 20% by weight, relative to the total weight of the composition.

Needless to say, a person skilled in the art will take care to select this or these optional additional compound(s) and/or the amounts thereof such that the cosmetic properties intrinsically associated with the composition in accordance with the disclosure are not, or are not substantially, adversely affected by the envisioned addition(s).

The latherability of the compositions according to the disclosure, characterized by a foam height, can be greater than 75 mm, for example greater than 100 mm, measured according to the amended Ross-Miles method (NF T 73-404/ISO696).

The amendments to the Ross-Miles method are the following:

The measurement is performed at a temperature of 22° C. with osmosed water. The concentration of the solution is 2 g/l. The height of the drop is 1 m. The amount of composition that is dropped is 200 ml. The 200 ml of composition falls into a measuring cylinder with a diameter of 50 mm and containing 50 ml of the test composition. The measurement is taken 5 minutes after stopping the flow of the composition.

These compositions may be in the form of, but are not limited to, more or less thickened liquids, creams or gels, mousses, waxes, water-in-oil (W/O) or oil-in-water (O/W) emulsions or multiple emulsions, and they are mainly suitable for washing and caring for keratin materials, for example the hair and the skin.

A subject of the disclosure is also a process for washing and conditioning keratin materials, such as the hair, which comprises applying to said wet keratin materials an effective amount of a composition as defined above, and then rinsing with water after an optional leave-in time.

The compositions according to the disclosure are, in at least one embodiment, used as shampoos for washing and conditioning the hair, and they may be applied, in this case, to wet hair in amounts that are suitable to wash it, and the lather generated by massaging or rubbing with the hands is then removed after an optional leave-in time, by rinsing with water, the operation optionally being repeated at least one time.

The compositions in accordance with the disclosure may also be used as shower gels for washing and conditioning the hair and/or the skin, wherein case they are applied to the wet skin and/or hair and are rinsed off after application.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

Concrete but non-limiting examples illustrating the disclosure are now given. The active materials are given in percentages.

EXAMPLES 1 to 4

The shampoo compositions below in accordance with the disclosure were prepared:

|  | In g AM | | | |
| --- | --- | --- | --- | --- |
|  | 1 | 2 | 3 | 4 |
| Cocoglucoside [1] | 5 | 5 | 5 | 5 |
| Cocoamidopropyl betaine [2] | 5.4 | 5.4 | 5.4 | 5.4 |
| Sodium lauryl ether (5 OE) carboxylate [3] | 3 | 3 | 3 | 3 |
| Sodium lauryl ether sulfate [4] | 4 | 4 | 4 | 4 |
| Polyquaternium-6 [5] | 0.4 | 0.4 | 0.4 | 0.4 |
| Polydimethylsiloxane (Dimethicone) [6] | 2.6 | 1 | 0.5 | 0.1 |
| Preserving agent | qs | qs | qs | qs |
| Fragrance | qs | qs | qs | qs |
| Citric acid | qs pH 6.5 | qs pH 6.5 | qs pH 6.5 | qs pH 6.5 |
| Water qs | 100 g | 100 g | 100 g | 100 g |

[1] PLANTACARE ® 818 UP sold by Cognis
[2] DEHYTON ® AB 30 sold by Cognis
[3] AKYPO ® RLM 45 CA sold by KAO
[4] TEXAPON ® N 702 sold by Cognis
[5] MERQUAT ® 100 sold by Nalco
[6] DC 200 Fluid 60000 CS sold by Dow Corning 1 gram of each formula was applied to a lock of natural brown Caucasian hair 25 cm long, weighing 2.7 g.

The locks were massaged for 15 seconds, left to stand for 5 minutes and then rinsed for 10 seconds (water at 30° C./flow rate 30 l/h) and finally combed. The wet locks were then dried under a hood for 30 minutes at 70° C.

The preceding operations were repeated twice.

The shampoo washes performed according to the disclosure showed very good working qualities (flash foaming, rinsability, quality of the feel of the fiber after rinsing).

An assay of the silicone was performed on the dried locks.

The assay of the amount of deposited silicone was performed by FTIR spectroscopy directly on the locks of hair using an ATR Zn—Se crystal. The amount of deposited silicone is defined by the absorbance measured on one of the characteristic absorption bands of silicones. The band located at 1262 $cm^{-1}$ was chosen to perform the measurement.

The absorbance intensity measured on this characteristic band was set at 1 for the control shampoo. This unit constitutes the arbitrary measuring unit (A.U.).

The control shampoo was constituted by a commercial composition containing a combination of anionic and amphoteric surfactants, a cationic polymer and the same dimethicone at a concentration of 2.6% identical to that of the composition of Example 1. The control shampoo was applied under the same conditions as the compositions according to the disclosure.

Results:

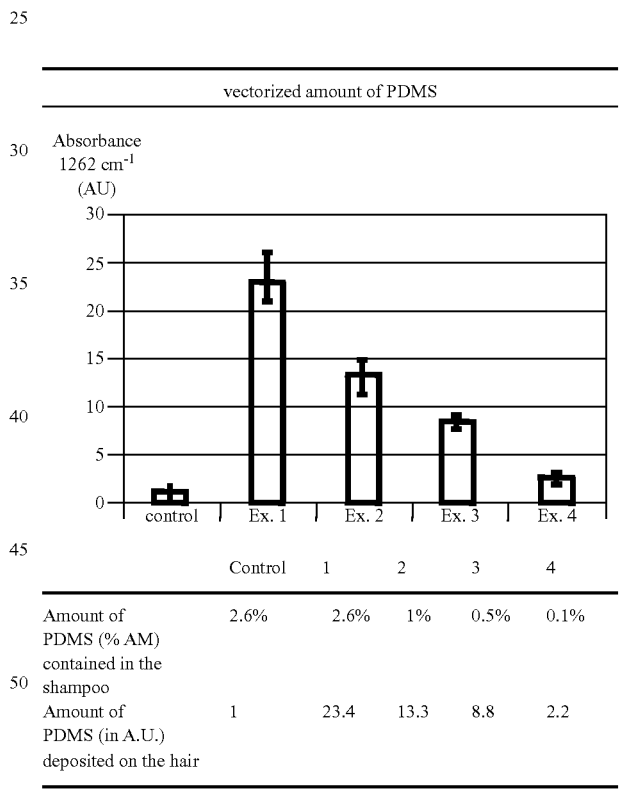

| | Control | 1 | 2 | 3 | 4 |
| --- | --- | --- | --- | --- | --- |
| Amount of PDMS (% AM) contained in the shampoo | 2.6% | 2.6% | 1% | 0.5% | 0.1% |
| Amount of PDMS (in A.U.) deposited on the hair | 1 | 23.4 | 13.3 | 8.8 | 2.2 |

As shown by the preceding results, the shampoo according to the disclosure (Ex. 1) makes it possible to vectorize more than 20 times the amount of silicone deposited by the control shampoo for an equivalent concentration of silicone in the compositions (2.6% AM).

It is also noted that by reducing in the compositions according to the disclosure (Ex. 4) the concentration of silicone 26-fold (Ex. 4) compared to the control composition, the amount of silicone vectorized by the composition according to the disclosure was still twice as much as the amount deposited by the control shampoo.

The compositions according to the disclosure afforded the same cosmetic benefit using much less silicone.

EXAMPLE 5

The shampoo composition below in accordance with the disclosure was prepared:

|  | 5 |
|---|---|
| Cocoglucoside [1] | 5 g AM |
| Cocoamidopropylbetaine [2] | 5.4 g AM |
| Sodium lauryl ether (5 OE) carboxylate [3] | 3 g AM |
| Sodium lauryl ether sulfate [4] | 4 g AM |
| Polyquaternium 6 [5] | 0.8 g AM |
| Red 7 [7] | 1 |
| Preserving agent | qs |
| Fragrance | qs |
| Citric acid | qs pH 6.5 |
| Water | qs 100 g |

[7] Pigment UNIPURE ® Red LC 3079 sold by LCW 1 gram of the preceding formulation was applied to a lock of natural Caucasian hair containing 90% white hairs, 25 cm long, weighing 2.7 g.

The lock was massaged for 15 seconds, left to stand for 5 minutes and then rinsed for 10 seconds (water at 30° C./flow rate 30 l/h) and finally combed. The wet lock was then dried under a hood for 30 minutes at 70° C.

The control shampoo was constituted by the composition containing detergent surfactants, a cationic polymer and a dimethicone, to which has been added 1% AM of the same red pigment as that contained in the composition according to the disclosure. The control shampoo was applied under the same conditions as the composition according to the disclosure.

The coloration of the locks of hair treated with the composition of the disclosure was much greater for an equivalent concentration of pigment than that of the hair treated with the control shampoo.

It was also noted that the transfer of pigments onto the skin with the composition of the disclosure was low, despite the large amount of pigment deposited onto the keratin fiber.

What is claimed is:

1. A detergent cosmetic composition for keratin materials, which comprises, in a cosmetically acceptable aqueous medium, (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, chosen from copolymers and homopolymers comprising, as the main constituent of the chain, units chosen from formulas (5) and (5'):

$$-(CH_2)t-CR_{12} \diagdown \begin{array}{c}(CH_2)k\\ \end{array} \diagup C(R_{12})-CH_2- \atop H_2C \diagdown \begin{array}{c}\\ \end{array} \diagup CH_2 \atop N^+ \; Y^- \atop R_{10} \; R_{11}$$ (5)

$$-(CH_2)t-CR_{12} \diagdown \begin{array}{c}(CH_2)k\\ \end{array} \diagup C(R_{12})-CH_2- \atop H_2C \diagdown \begin{array}{c}\\ \end{array} \diagup CH_2 \atop N \atop R_{10}$$ (5')

wherein k and t are equal to 0 or 1, the sum k+t being equal to 1;

$R_{12}$ is chosen from a hydrogen atom and a methyl radical;

$R_{10}$ and $R_{11}$, which may be identical or different, are chosen from alkyl groups comprising from 1 to 6 carbon atoms, hydroxyalkyl groups wherein the alkyl group, comprises from 1 to 5 carbon atoms, and lower ($C_1$-$C_4$) amidoalkyl groups, or $R_{10}$ and $R_{11}$, together with the nitrogen atom to which they are attached, are chosen from heterocyclic groups;

and $Y^-$ is an anion chosen from bromide, chloride, acetate, borate, citrate, tartrate, bisulfate, bisulfite, sulfate and phosphate; and (F) at least one agent that is beneficial to keratin materials, other than the at least one cationic polymer of (E), chosen from oils sweet almond oil, avocado oil, castor oil, olive oil, sunflower oil, wheatgerm oil, sesame seed oil, groundnut oil, grapeseed oil, soybean oil, rapeseed oil, safflower oil, coconut oil, corn oil, hazelnut oil, shea butter, palm oil, apricot kernel oil, beauty-leaf oil, perhydrosqualene, liquid paraffin, liquid petroleum jelly, and mixtures thereof;

wherein the sulfate, sulfonate or phosphate anionic surfactant/amphoteric surfactant weight ratio is in a range from 0.1 to 2; wherein said composition is a rinse out composition capable of increasing the deposition of said beneficial agent onto said keratin materials.

2. The composition according to claim 1, wherein the total amount of surfactant is in an amount ranging from 4% to 50% by weight, relative to the total weight of the composition.

3. The composition according to claim 2, wherein the total amount of surfactant is in an amount ranging from 8% to 25% by weight, relative to the total weight of the composition.

4. The composition according to claim 1, wherein the at least one anionic surfactant of (A) is present in an amount ranging from 1% to 50% by weight, relative to the total weight of the composition.

5. The composition according to claim 4, wherein the at least one anionic surfactant of (A) is present in an amount ranging from 2% to 25% by weight, relative to the total weight of the composition.

6. The composition according to claim 1, wherein the at least one carboxylic anionic surfactant other than the at least one anionic surfactant of (A) is present in an amount ranging from 0.5% to 15% by weight, relative to the total weight of the composition.

7. The composition according to claim 6, wherein the at least one carboxylic anionic surfactant other than the at least one anionic surfactant of (A) is present in an amount ranging from 1.5% to 8% by weight, relative to the total weight of the composition.

8. The composition according to claim 1, wherein the at least one amphoteric or zwitterionic surfactant is present in an amount ranging from 0.1% to 20% by weight, relative to the total weight of the composition.

9. The composition according to claim 8, wherein the at least one amphoteric or zwitterionic surfactant is present in an amount ranging from 2% to 10% by weight, relative to the total weight of the composition.

10. The composition according to claim 1, wherein the at least one alkylpolyglycoside nonionic surfactant is present in an amount ranging from 0.1% to 20% by weight, relative to the total weight of the composition.

11. The composition according to claim 10, wherein the at least one alkylpolyglycoside nonionic surfactant is present in an amount ranging from 1% to 15% by weight, relative to the total weight of the composition.

12. The composition according to claim 1, wherein the sulfate, sulfonate or phosphate anionic surfactant/carboxylic anionic surfactant weight ratio is in a range from 0.5 to 5.

13. The composition according to claim 1, wherein the carboxylic anionic surfactant/amphoteric surfactant weight ratio is in a range from 0.1 to 10.

14. The composition according to claim 13, wherein the carboxylic anionic surfactant/amphoteric surfactant weight ratio is in a range from 0.3 to 2.

15. The composition according to claim 1, wherein the at least one alkylpolyglucoside nonionic surfactant is chosen from the following general formula:

$$R_1O—(R_2O)_t(G)_v \qquad (4)$$

wherein $R_1$ is chosen from linear or branched alkyl and alkenyl radicals comprising from 8 to 24 carbon atoms, and alkylphenyl radicals, wherein the linear or branched alkyl radical comprises from 8 to 24 carbon atoms, $R_2$ is an alkylene radical comprising from 2 to 4 carbon atoms, G is a sugar unit comprising 5 or 6 carbon atoms, t is a value ranging from 0 to 10, and v is a value ranging from 1 to 15.

16. The composition according to claim 1, wherein the at least one agent that is beneficial to keratin materials other than the at least one cationic polymer of (E) is present in an amount ranging from 0.001% to 20%, relative to the total weight of the composition.

17. The composition according to claim 16, wherein the at least one agent that is beneficial to keratin materials other than the at least one cationic polymer of (E) is present in an amount ranging from 0.01% to 10% by weight, relative to the total weight of the composition.

18. The composition according to claim 1, wherein the at least one cationic polymer with a cationic charge density of greater than or equal to 4 meq./g is present in an amount ranging from 0.01% to 10% by weight, relative to the total weight of the composition.

19. The composition according to claim 18, wherein the at least one cationic polymer with a cationic charge density of greater than or equal to 4 meq./g is present in an amount ranging from 0.1% to 5% by weight, relative to the total weight of the composition.

20. A method for cleansing and/or removing makeup from keratin materials comprising the application of a detergent cosmetic composition, which comprises, in a cosmetically acceptable aqueous medium, (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, chosen from copolymers and homopolymers comprising, as the main constituent of the chain, units chosen from formulas (5) and (5'):

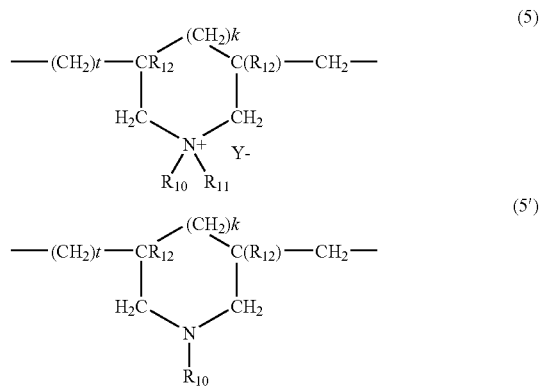

wherein k and t are equal to 0 or 1, the sum k +t being equal to 1;

$R_{12}$ is chosen from a hydrogen atom and a methyl radical;

$R_{10}$ and $R_{11}$, which may be identical or different, are chosen from alkyl groups comprising from 1 to 6 carbon atoms, hydroxyalkyl groups wherein the alkyl group, comprises from 1 to 5 carbon atoms, and lower ($C_1$-$C_4$) amidoalkyl groups, or $R_{10}$ and $R_{11}$, together with the nitrogen atom to which they are attached, are chosen from heterocyclic groups;

and $Y^-$ is an anion chosen from bromide, chloride, acetate, borate, citrate, tartrate, bisulfate, bisulfite, sulfate and phosphate; and (F) at least one agent that is beneficial to keratin materials, other than the at least one cationic polymer of (E), chosen from oils sweet almond oil, avocado oil, castor oil, olive oil, sunflower oil, wheatgerm oil, sesame seed oil, groundnut oil, grapeseed oil, soybean oil, rapeseed oil, safflower oil, coconut oil, corn oil, hazelnut oil, shea butter, palm oil, apricot kernel oil, beauty-leaf oil, perhydrosqualene, liquid paraffin, liquid petroleum jelly, and mixtures thereof;

wherein the sulfate, sulfonate or phosphate anionic surfactant/amphoteric surfactant weight ratio is in a range from 0.1 to 2; wherein said composition is a rinse out composition capable of increasing the deposition of said beneficial agent on to said keratin materials.

21. A process for washing and conditioning keratin materials, comprising applying to said keratin materials a composition, which comprises, in a cosmetically acceptable aqueous medium, (A) at least one anionic surfactant comprising at least one group chosen from sulfate, sulfonate and phosphate, (B) at least one carboxylic anionic surfactant other than the at least one anionic surfactant of (A), (C) at least one amphoteric or zwitterionic surfactant, (D) at least one alkylpolyglycoside nonionic surfactant, (E) at least one cationic polymer with a cationic charge density of greater than or equal to 4 meq./g, chosen from copolymers and homopolymers comprising, as the main constituent of the chain, units chosen from formulas (5) and (5'):

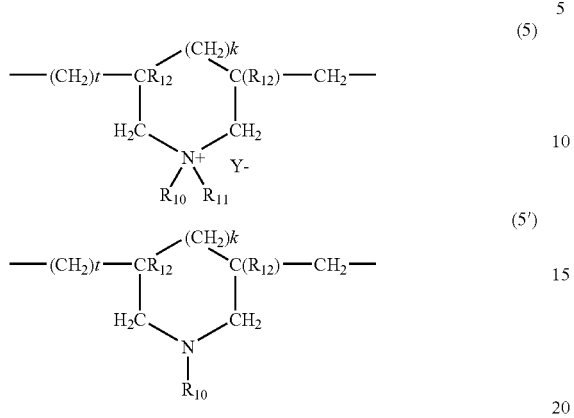

(5)

(5')

wherein k and t are equal to 0 or 1, the sum k +t being equal to 1;
$R_{12}$ is chosen from a hydrogen atom and a methyl radical;
$R_{10}$ and $R_{11}$, which may be identical or different, are chosen from alkyl groups comprising from 1 to 6 carbon atoms, hydroxyalkyl groups wherein the alkyl group, comprises from 1 to 5 carbon atoms, and lower ($C_1$-$C_4$) amidoalkyl groups, or $R_{10}$ and $R_{11}$, together with the nitrogen atom to which they are attached, are chosen from heterocyclic groups;

and $Y^-$ is an anion chosen from bromide, chloride, acetate, borate, citrate, tartrate, bisulfate, bisulfite, sulfate and phosphate; and (F) at least one agent that is beneficial to keratin materials, other than the at least one cationic polymer of (E), chosen from oils sweet almond oil, avocado oil, castor oil, olive oil, sunflower oil, wheatqerm oil, sesame seed oil, groundnut oil, qrapeseed oil, soybean oil, rapeseed oil, safflower oil, coconut oil, corn oil, hazelnut oil, shea butter, palm oil, apricot kernel oil, beauty-leaf oil, perhydrosqualene, liquid paraffin, liquid petroleum jelly, and mixtures thereof;

wherein the sulfate, sulfonate or phosphate anionic surfactant/amphoteric surfactant weight ratio is in a range from 0.1 to 2; wherein said composition is a rinse out composition capable of increasing the deposition of said beneficial agent on to said keratin materials, and then in rinsing said keratin materials with water, wherein said composition may optionally be left on said keratin materials for a leave-in time before rinsing.

22. The process according to claim 21, wherein the keratin materials are hair.

* * * * *